United States Patent [19]

Washington et al.

[11] 4,198,854
[45] Apr. 22, 1980

[54] METHOD AND APPARATUS FOR MEASURING POROSITY

[75] Inventors: James M. Washington; Gerald H. Crowther; Robert T. Gaudlitz, all of Richmond, Va.

[73] Assignee: Philip Morris Incorporated, New York, N.Y.

[21] Appl. No.: 967,250

[22] Filed: Dec. 7, 1978

[51] Int. Cl.² ............................................. G01M 3/02
[52] U.S. Cl. ..................................................... 73/38
[58] Field of Search .......................... 73/38, 37.7, 159

[56] References Cited

U.S. PATENT DOCUMENTS 2,861,451  11/1958  Emmons ................................. 73/38

FOREIGN PATENT DOCUMENTS 980058  1/1965  United Kingdom ........................ 73/38

Primary Examiner—Gerald Goldberg
Assistant Examiner—Joseph W. Roskos
Attorney, Agent, or Firm—Watson, Leavenworth, Kelton & Taggart

[57] ABSTRACT

A practice for measuring porosity wherein a plurality of medium flows of different volumetric flow rates are provided to a predetermined area of a material under test in dependence upon the pressure difference thereacross and wherein certain measured pressure/differences and their corresponding flow rates are employed to determine the material porosity.

44 Claims, 8 Drawing Figures

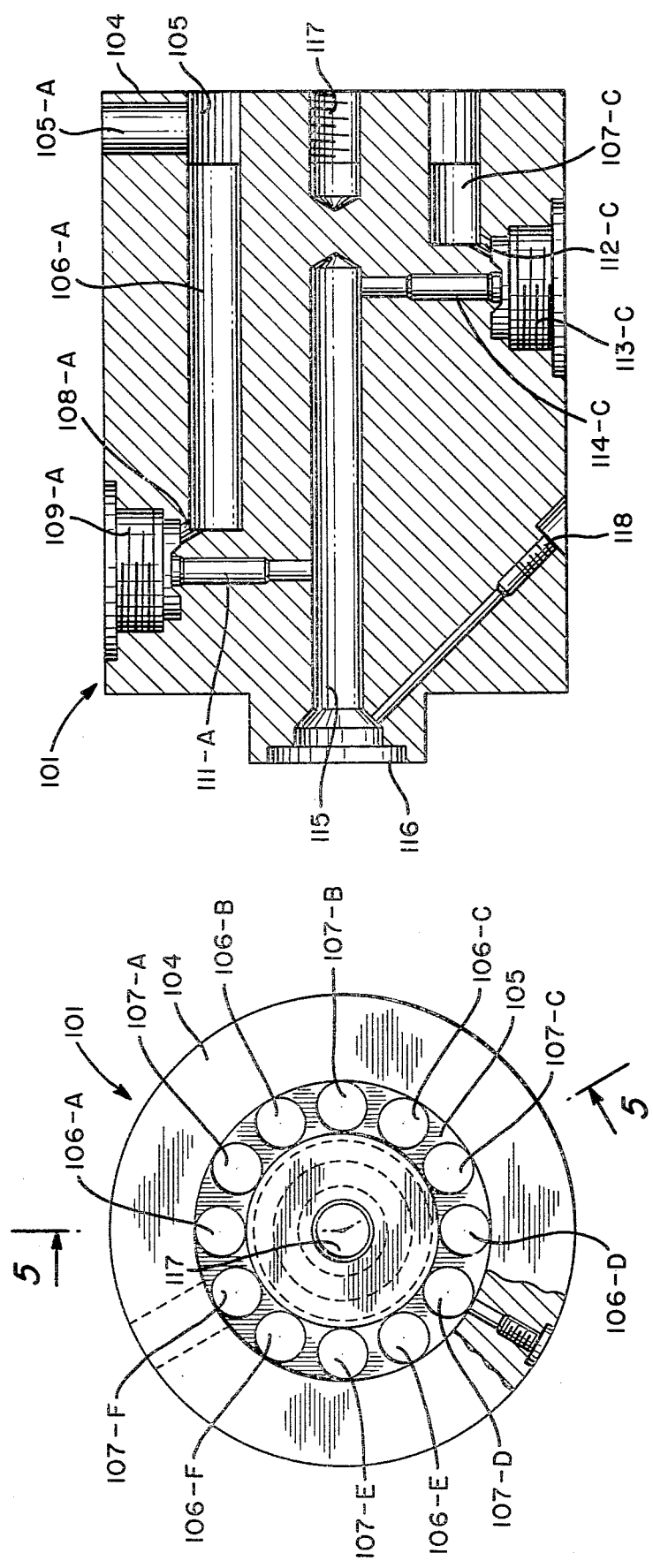

METHOD AND APPARATUS FOR MEASURING POROSITY

BACKGROUND OF THE INVENTION

This invention pertains to measuring techniques and, more particularly, to porosity measuring techniques.

The measurement of the porosity of materials is of interest in many different manufacturing fields. One such field is the field of cigarette manufacture wherein the need to accurately measure cigarette paper porosity is essential to the tailoring of cigarettes to meet varying smoking requirements.

In the past, the only paper having a significant effect on cigarette performance was the paper surrounding the tobacco column or rod. Typically, the porosity of such rod-wrapping paper was measured using the so-called Greiner method or technique. The Greiner method gave a measure of cigarette paper porosity in terms of units of time and was carried out by measuring the time that elapsed during the flow through a known area of the paper of a specific volume of air traveling at a variable volumetric rate.

Recently, however, due to the cigarette industry's efforts to develop cigarette constructions having improved smoke dilution characteristics, a variety of new papers have been developed whose porosities vary over an extremely broad range. Typically, these new papers may be high porosity rod-wrapping papers, or porous papers used to wrap filter plugs, or porous or artificially perforated tipping papers i.e., papers which surround the filter plug wrap and which connect the filter plug to the cigarette rod-wrap. Owing to the high values and broad range of porosities possessed by these new papers, the measurement of these porosities using the Greiner method has proven unsatisfactory. As a result, new porosity measuring techniques have been developed which provide a measurement of paper porosity in terms of so-called Coresta units. A Coresta unit is a measure of the volume of air in cubic centimeters passing per unit time (minute) through a unit area (1.0 square centimeter) of a paper at a predetermined pressure equivalent to the pressure exerted by a 10 centimeter column of water.

In one prior art procedure for measuring paper porosity in terms of Coresta, air is passed through a known cross-sectional area of the paper and the volumetric flow rate of the air is continuously varied until the pressure drop or difference across the cross-sectional area is equivalent to the pressure exerted by a 10 centimeter column of water. To measure porosities over a wide range with this procedure several flow-measuring instruments are required. Additionally, a pressure regulator is required which is capable of providing a constant pressure drop over a wide range of flow velocities. Owing to these requirements, this measurement technique has not found widespread use where porosity measurements over a broad range are desired.

In another prior art procedure for measuring Coresta porosity, air is passed through a known cross-sectional area of the paper in such a manner as to maintain the volumetric flow rate of the air constant. In this procedure, the pressure drop across the cross-sectional area is measured for the constant flow rate, and this measured drop is extrapolated to determine what the flow rate would be for a pressure drop equivalent to a 10 centimeter column of water. Again this approach has not proven entirely succesful for measuring porosities extending over a relatively wide band or range.

It is therefore a broad object of the present invention to provide an improved method and apparatus for measuring the porosity of materials.

It is a further object of the present invention to provide a method and apparatus for accurately and rapidly measuring the porosity of materials whose porosities vary over a wide band.

It is a further object of the present invention to provide a method and apparatus for measuring the porosity of papers used in the construction of cigarettes.

SUMMARY OF THE INVENTION

In accordance with the principles of the present invention, the above and other objectives are realized in a measuring practice wherein a plurality of medium flows having different flow rates are provided and are selectively applied to a predetermined area of a material in dependence on the pressure difference across such area. The flow rates of the medium flows resulting in certain of the measured pressure differences are then employed with these pressure differences to determine a porosity value for the material which closely approximates its actual porosity value.

More particularly, application of the medium flows is carried out until a first set of one or more medium flows is determined which provides a first pressure difference across the predetermined material area which is above a predetermined pressure difference to a lesser degree than the pressure difference resulting from any other set of one or more medium flows. Likewise, application of the medium flows is further carried out until a second set of the medium flows is determined which provides a second pressure difference across the predetermined material area which is below the aforesaid predetermined pressure difference to a lesser degree than the pressure difference resulting from any other set of one or more medium flows. Having determined the first and second sets of medium flows and the first and second measured pressure differences corresponding thereto, the flow rates of the medium flows of these sets and the measured pressure differences are then used to formulate an average flow per unit time per unit pressure difference which is then employed to a calculated or determine the porosity of the material.

In a further aspect of the present invention, a predetermined pattern or sequence of application of the medium flows for realizing an efficient and rapid determination of the first and second sets of medium flows is disclosed.

In yet a further aspect of the present invention, a medium flow generating and conveying assembly which is of compact construction and particularly suitable for wide band porosity measurement is also disclosed.

BRIEF DESCRIPTION OF THE DRAWINGS

The above and other features and aspects of the present invention will become more apparent upon reading the following detailed description in conjunction with the accompanying drawings, in which:

FIG. 4 illustrates a rear view of the assembly of FIG. 3 with the actuating valve assemblies removed;

FIG. 5 shows a cross-sectional view of the assembly of FIG. 4 taken along the line 5—5 in FIG. 4.

DETAILED DESCRIPTION

Figure 1A:
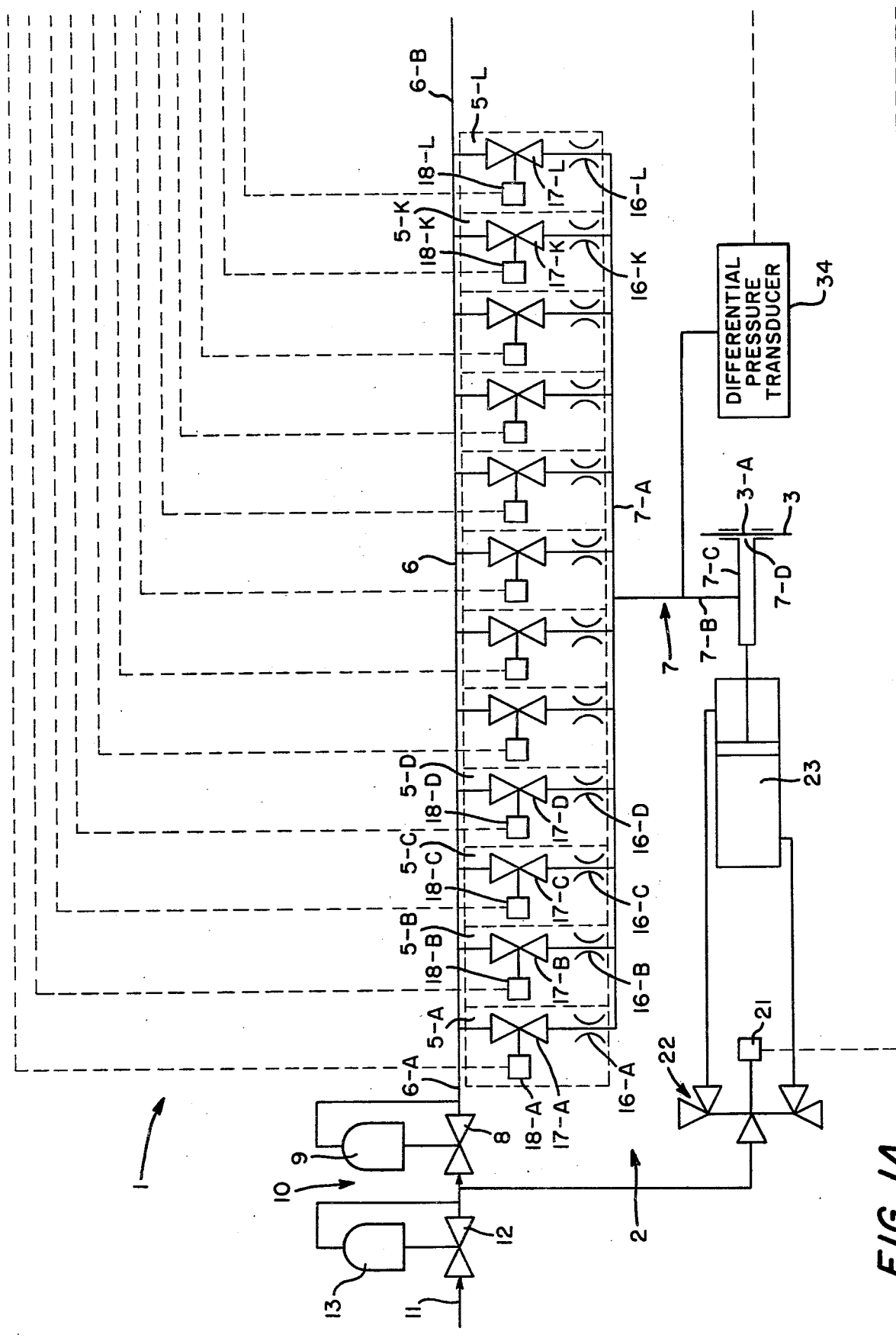
FIGS. 1A and 1B illustrate in schematic fashion a porosity measuring structure embodying the method and apparatus of the present invention.
Figure 1B:
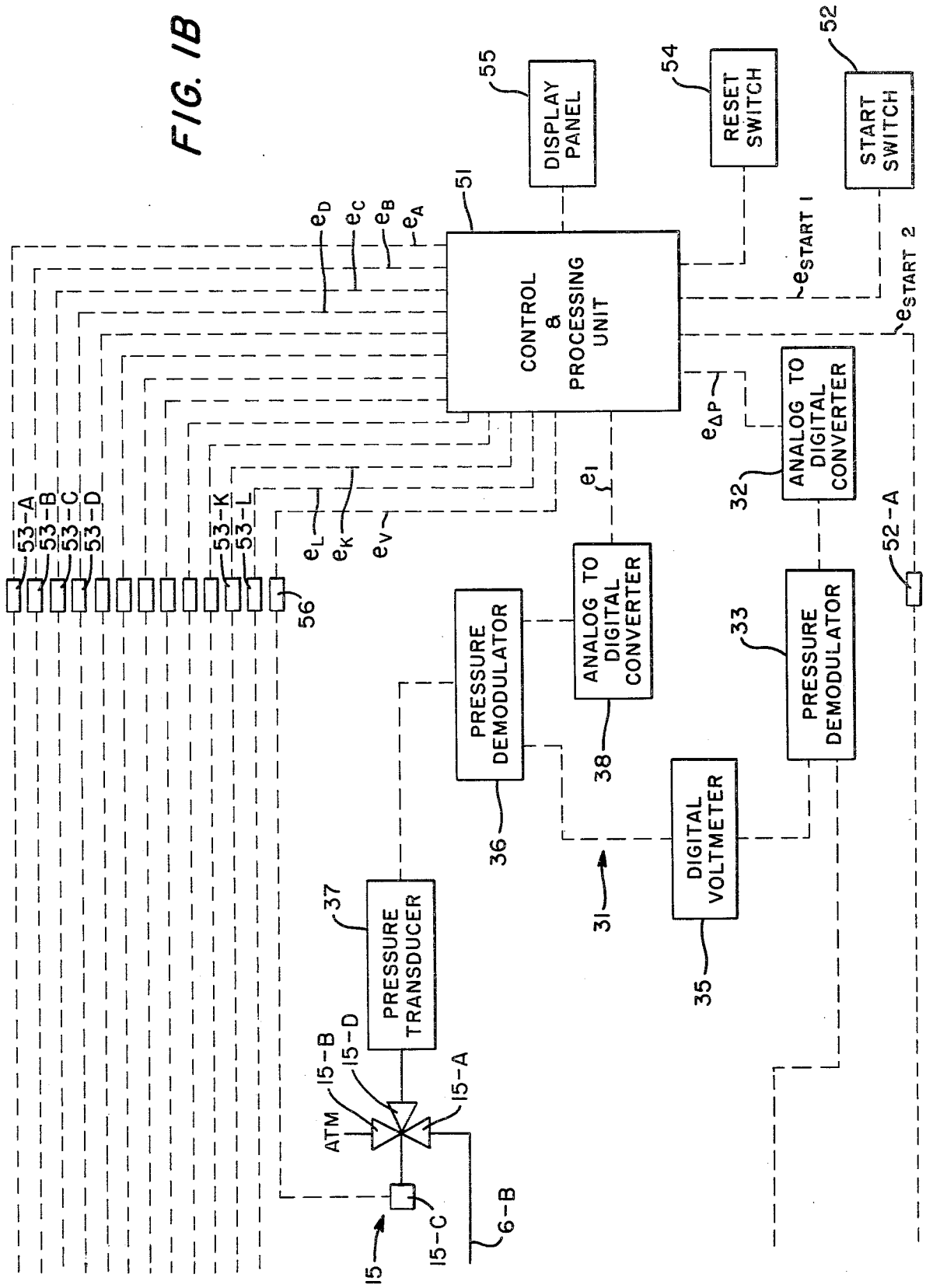

FIGS. 1A and 1B show schematically a porosity measuring structure 1 embodying the method and apparatus of the present invention. The measuring structure 1 comprises a medium flow generating and conveying assembly 2 which is adapted to generate and convey a plurality of medium flows, such as, for example, air flows to a material 3 whose porosity is to be measured. The material 3, typically, might be cigarette paper which is inherently porous or has been made porous by perforating.

As shown, the assembly 2 comprises a plurality of openable passage means depicted, illustratively, as means 5-A through 5-L, which are connected in parallel between a medium flow inlet manifold 6 and a medium flow outlet manifold 7. An initial section 7-A of the manifold 7 communicates directly with the openable passage means 5-A through 5-L. This initial manifold section is further coupled to an intermediate section 7-B of the manifold which, in turn, connects to a terminal section 7-C of the manifold. The latter manifold section has an open end 7-D which faces the material 3 and which conveys medium flow from the passage means 5-A through 5-L to a predetermined area 3-A of the material.

The inlet manifold 6 receives medium flow for coupling to the passage means 5-A through 5-L through its input end 6-A which is connected to an input manifold pressure regulator 10. Regulator 10 comprises a valve 8 and a pressure control mechanism 9. The control effected by the mechanism 9 ensures that the medium in the manifold 6 is maintained at a constant pressure which might, typically, be 40 psia. A medium flow primary supply line 11 supplies medium flow at a constant pressure to the valve 8 through a medium flow primary pressure regulator comprised of a control mechanism 13 and a valve 12. The primary regulator (12, 13) can be a conventional component and, typically, might be a Moore 40-50 type regulator. Likewise, the absolute pressure regulator 10 can also be a standard component such as, for example, of the type manufactured by Moore Products under part No. 43-50.

The output of end 6-B of the input manifold 6 is coupled to one input valve section 15-A of a three-way valve 15 whose other input valve section is open to the atmosphere. The valve 15 is further provided with a control assembly 15-C for selectively connecting the input valve sections 15-A and 15-B to the common output valve section 15-D.

As illustrated, the passage means 5-A through 5-L comprise respective orifice members 16-A through 16-L. These orifice members are connected directly to the output manifold 7 and are connected to the input manifold 6 through respective control valves 17-A through 17-L. Respective actuating members 18-A through 18-L are provided for opening and closing the control valves 17-A through 17-L.

In accordance with the invention, the passage means 5-A through 5-L are further adapted through appropriate configuration of their respective orifice members to provide medium flows at the output manifold 7, for a given constant flow pressure at the input manifold 6, of differing and, in the present illustrative case, increasing predetermined flow velocities in proceeding from the means 5-A to the means 5-L. Thus, the member 5-A will couple medium from the input manifold 6 to the output manifold 7 at a first predetermined flow velocity $F_A$, the member 5-B at a second predetermined flow velocity $F_B$ greater than $F_A$ and the remaining members at the respective predetermined flow velocities $F_C$, $F_D$, $F_E$, $F_F$, $F_G$, $F_H$, $F_I$, $F_K$ and $F_L$, where $F_L > F_K > F_J > F_I > F_H > F_G > F_F > F_E > F_D > F_C > F_B$. In a typical case, the ratio of each of these flow velocities to its immediately preceding flow velocity might be in the range of 1.5 to 3.0, a ratio of about 2.0 being preferable. Of course, the actual determination of these ratios for any particular case will depend on the measurement accuracy and range desired.

Through suitable activation of the passage means valves 17-A through 17-L, the assembly 2 can be made to generate and convey to the predetermined area 3-A of the material 3 medium flows having any one of the flow rates $F_A$ through $F_L$, as well as any one of a number combinations of these flow rates. When more than one medium flow is conveyed to the output manifold 7, the medium flows have an additive effect and, thus, combine to result in a single medium flow having a flow rate equal to the sum of the rates of the individual flows.

In accordance with the invention, activation of the valves 17-A through 17-L is carried out to provide medium flows which result in pressure differences across the area 3-A which, along with the medium flow rates, can be used to derive an accurate representation of the porosity $P_r$ of the material 3. More specifically, the desired activation is brought about by the provision in the structure 1 of a central control and processing unit 51 having computation, storage and sequential operation capabilities.

In particular, the unit 51 provides selection control digital signals $e_A$ through $e_L$ which are coupled to and control the respective valve actuating members 18-A through 18-L of the passage means 5-A through 5-L. In particular, the signals $e_A$ through $e_L$ cause operation of respective relays 53-A through 53-L which connect power sources (not shown) to the actuating members 18-A through 18-L for turning same on.

The signals $e_A$ through $e_L$ are generated by the unit 51 in response to a signal $e_{\Delta P}$ which represents the pressure difference $\Delta P$ across the area 3-A and which is provided an an output of an interface and detection unit 31. The signal $e_{\Delta P}$ is formed by an analog-to-digital converter 32 which is fed a demodulated analog signal corresponding to the pressure difference $\Delta P$ from a pressure demodulator 33. The demodulator 33 generates this demodulated signal in response to the pressure difference output signal of a differential pressure transducer 34. The transducer 34 has one input port connected into the output manifold section 7-B for monitoring the pressure on the output manifold side of the material area 3-A and another input port which monitors atmospheric pressure, which is the pressure on the other side of the area 3-A.

A second demodulator 36 selectively receives atmospheric and input manifold pressure information from a second transducer 37 which senses the pressure at the output valve section 15-D of the two-way valve 15 of the assembly 2. The demodulator 36 supplies this information through a further analog-to-digital converter 38 as a further digital input signal $e_1$ to the processing unit 51. Tthe detection unit 31 is further provided with a digital voltmeter 35 for selectively monitoring the operation of the demodulators 33 and 36.

An input start signal $e_{start1}$ is fed to the unit 51 from a start switch 52 which is activated by an operator when a porosity determination is to be made. Once the $e_{start1}$ signal is received from start switch 52, unit 51 establishes a start signal $e_{start2}$ which activates a solid state relay 52-A. The relay 52-A connects a power source (not shown) to bring the end of the terminal manifold section 7-C into close proximity with the material 3. This is effected by operation of an activating member 21 which controls a differential valve configuration 22. The valve configuration 22 provides medium flow for driving a pressure cylinder 23 connected to the manifold section 7-C. The valve 22, in turn, is fed medium flow from the source line 11 through the valve 12.

The processing unit 51 is also provided with a reset switch 54 and with a display panel 55. The reset switch enables the unit to be set to a measurement operating state by resetting of the outputs $e_A$ to $e_L$ and by clearing the display panel 55. The latter panel is used to display the porosity value determined by the unit.

As above-indicated, the processing unit 51 possesses storage, computation and sequential operation capabilities. Typically, the unit 51 might comprise a conventional programmable microprocessor or digital computer having plural output and input capabilities. A particular microprocessor might be Model No. SDK-80 manufactured by Intel Corporation. The demodulator units 33 and 36 can also be of a conventional type and might, for example, be Model No. CD101-4CT demodulators manufactured by Validyne Engineering Corporation. Similarly, analog-to-digital converters 32 and 38 can be of a standard type as can be the digital voltmeter 35. A typical analog-to-digital converter might be Model No. HX12BGC manufactured by Datel Systems, Inc.

As discussed above, the processing unit 51 computes the porosity $P_r$ of the medium 3 from measured pressure differences and corresponding medium flow rates determined through selective activation of the passage means valves 17-A through 17-L as a function of the differential pressure $\Delta P$. In accordance with the invention, the unit 51 is conditioned to provide such selective activation in a manner which results in fluid flows which provide first and second measured pressure difference values $\Delta P_{min}$ and $\Delta P_{max}$ which bear specific relationships to a reference or predetermined pressure difference value $\Delta P_{ref}$. More particularly, the measured pressure differences $\Delta P_{max}$ and $\Delta P_{min}$ correspond to the pressure differences which are above and below, respectively, the reference pressure difference $\Delta P_{ref}$ by the least amount. To arrive at these pressure differences, the selection control signals $e_A$ through $e_L$ of the unit 51 are varied to selectively open the passage means valves 17-A through 17-L until a set of one or more valves is determined which gives the pressure difference $\Delta P_{max}$ and further, until a set of one or more valves is determined which gives the pressure difference $\Delta P_{min}$. Such varying or changing of the signals $e_A$ through $e_L$ of the unit 51 can follow any one of a number of different patterns, although, as will be discussed hereinbelow, a unique activation pattern has been found which results in a rapid and efficient determination of these pressures.

During the selective opening and closing of the passage means valves, the processing unit 51 also continuously monitors the pressure difference values being generated via the input signal $e_{\Delta P}$. The values of $\Delta P_{max}$ and $\Delta P_{min}$ when reached are thus monitored and stored by the unit. Thereafter, as mentioned above, the unit uses these values and the flow rates $F_A$ through $F_L$ of the medium flows, which it also has stored, to determine the porosity $P_r$ of the paper 3. In particular, initial calculations are mady by the unit to derive minimum and maximum volumetric flows per unit time per unit pressure difference $Q_{min}$ and $Q_{max}$. The former is computed by dividing the composite or sum of the flow rates of the medium flows producing the pressure difference $\Delta P_{max}$ by $\Delta P_{max}$ and the latter by dividing the composite or sum of the flow velocities of the medium flows producing the pressure difference $\Delta P_{min}$ by $\Delta P_{min}$. The unit 51 then averages these computed values to determine an average volumetric flow per unit time per unit pressure difference $Q_{bar}$. This average value is then divided by the extent of the predetermined area 3-A to provide a measure of the average volumetric flow per unit time per unit pressure per unit area of the material 3. Finally, unit 51 calculates the porosity $P_r$ of the material 3 from the latter average referenced to the reference pressure difference $\Delta P_{ref}$ by multiplication by this pressure difference. In the present illustrative case, the unit 51 is adapted to provide a porosity in units of Coresta and thus multiplies the calculated average by a factor of 10. In this last calculation, the unit also provides compensation for any changes in atmospheric pressure and input manifold pressure by including compensating multipliers. The resultant Coresta porosity is then displayed at panel 55 for visual observation.

Figure 2A:
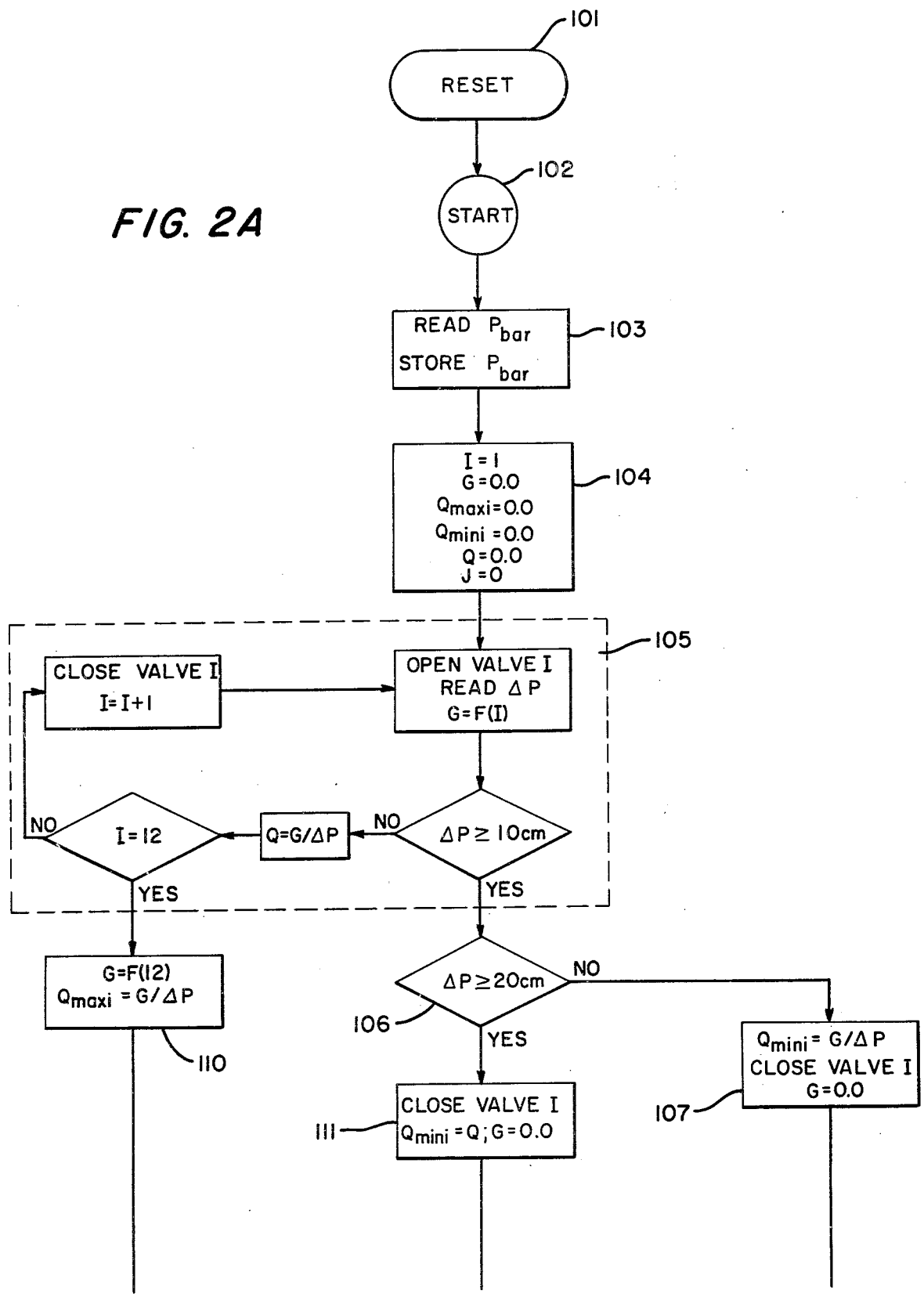
FIGS. 2A and 2B illustrate a flow chart showing a particular operating sequence carried out by the central control and processing unit of the structure of FIG. 1.
Figure 2B:
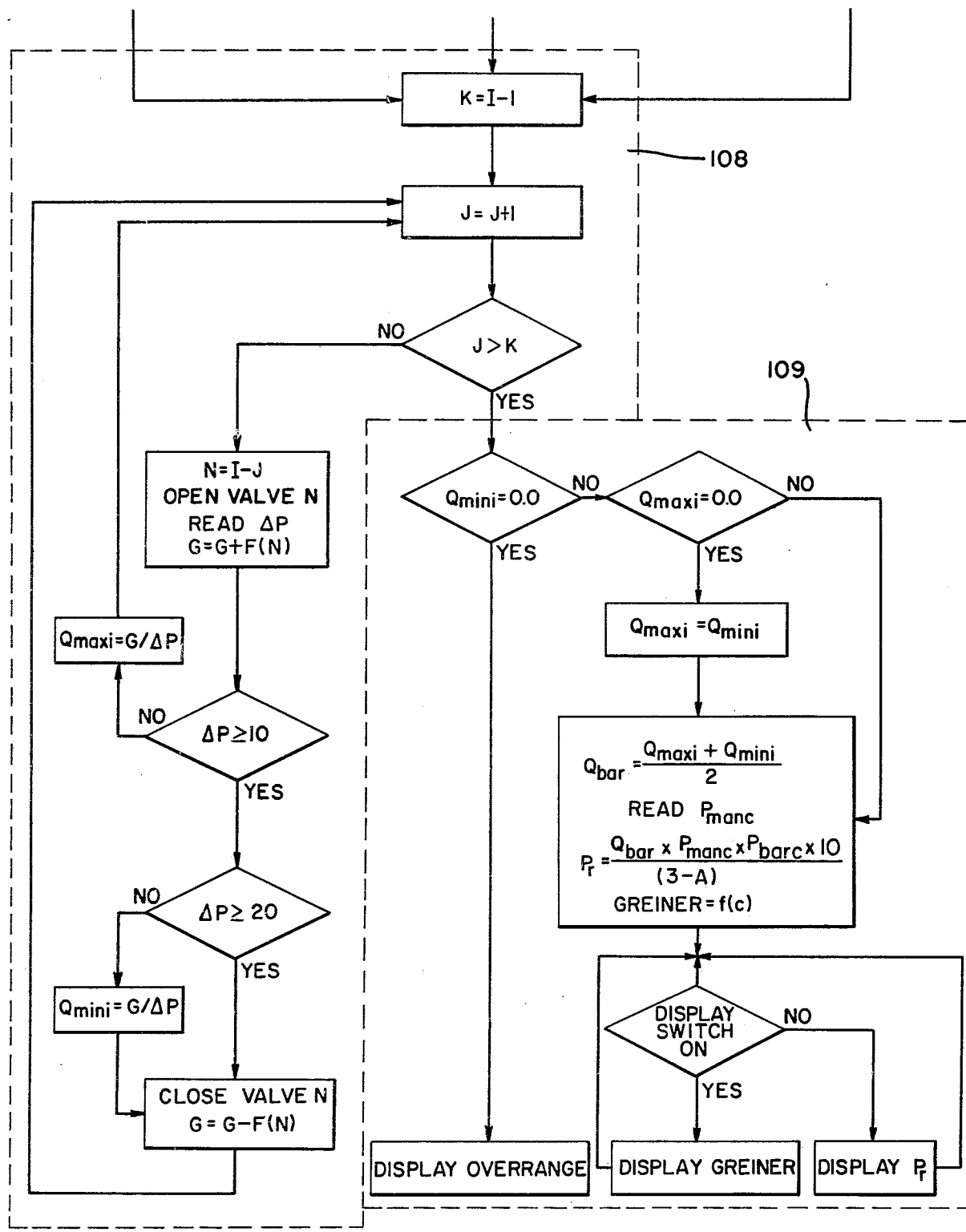

As noted above, the processing unit 51 in arriving at the pressure differences $\Delta P_{max}$ and $\Delta P_{min}$ can change the values of the signals $e_A$ through $e_L$ and, hence, activate the openable passage valves in any one of a number of operating patterns. FIGS. 2A and 2B depict a flow diagram showing the operating sequence of the unit 51 to arrive at a porosity value for the material 3 and including a highly advantageous pattern for activating the passage means valves. This pattern provides the values of $P_{max}$ and $\Delta P_{min}$ and, hence, the porosity $P_r$, in an expeditious and step saving manner.

More specifically, the operating sequence of the flow chart of FIGS. 2A and 2B can be viewed as defining two basic operating procedures for the unit 51. In a first operating procedure encompassing steps 101 through 108, 110 and 111, the values of $\Delta P_{max}$ and $\Delta P_{min}$ and the corresponding values of $Q_{min}$ and $Q_{max}$ are determined. In a second operating procedure encompassing step 109 these values are used to derive a porosity value or a signal indicating that the porosity being measured is out of the measurement range of the unit.

The first operating procedure is carried out employing the above-mentioned advantageous activating pattern for the passage means valves and will be initially discussed in general terms. The specific details of both procedures will then be discussed in detail.

The activating pattern defined in the first operating procedure includes two phases. In a first phase, the signals $e_A$ through $e_L$ open and close the valves 17-A through 17-L in the order of valves providing medium flows of increasing flow rate (i.e., from the valve 17-A to the valve 17-L). This sequential process continues until a valve is opened whose corresponding medium flow when applied to the material area 3-A results in a measured pressure difference $\Delta P$, which is above the reference $\Delta P_{ref}$. For present illustrative purposes, since Coresta porosity is being determined, the reference pressure difference $\Delta P_{ref}$ is equivalent to the pressure exerted by a 10 centimeter column of water (i.e., is depicted as 10 cm in the flow diagram).

At this point, the first phase of the activating pattern terminates, and an initial intermediate calculation of a minimum volumetric flow per unit time per unit pressure difference $Q_{mini}$ is calculated by dividing the flow velocity corresponding to the measured pressure difference, by such pressure difference. This initial intermediate value of $Q_{mini}$ is then stored, and the signals $e_A$ through $e_L$ changed so that the passage valve resulting in the measured pressure is closed.

The second phase of the first procedure then begins by further conditioning the signals $e_A$ through $e_L$ to sequentially open the passage valves in the order of valves of decreasing flow rate starting with the valve whose corresponding flow rate immediately precedes that of the valve that terminated the first phase. During this second phase, opened valves are maintained opened unless the flow medium resulting from opening a valve when conveyed to the area 3-A causes the pressure difference $\Delta P$ to again exceed the reference pressure difference $\Delta P_{ref}$. In such case, the valve is closed and the sequence of opening the valves of lesser flow rate continued.

When a particular valve is maintained opened during this second phase, an intermediate maximum volumetric flow per unit time per unit pressure difference $Q_{maxi}$ is calculated and then stored in place of any previously stored intermediate $Q_{maxi}$ value. This intermediate $Q_{maxi}$ value is determined by multiplying the reciprocal of the pressure difference occurring across the area 3-A during the opening of the particular valve (this pressure difference is the total pressure difference caused by the particular opened valve and by any previously maintained opened valves) by the flow rate corresponding to that pressure difference (again this is a sum of the flow rates of the particular opened valve and the previously maintained opened valve). A new intermediate $Q_{maxi}$ value is thus updated (i.e., calculated and stored) every time a valve is opened and maintained opened.

On the other hand, every time a particular valve is opened and then closed during this second sequence a new intermediate value of minimum flow per unit time per unit pressure difference $Q_{mini}$ is calculated and stored. This value, if calculated, replaces the initial intermediate $Q_{mini}$ value determined in the first phase or an intermediate value previously calculated in the second phase. As with $Q_{maxi}$, $Q_{mini}$ is updated every time another valve opens and closes. Moreover, it also is determined by multiplying the reciprocal of the pressure difference resulting from all the opened valves at the time of its occurrence by the sum of the flow velocities associated with these valves.

As can be appreciated, at the end of this second activating phase, the set of one or more valves remaining opened will be that set of one or more valves which results in a pressure difference which is the least below the reference pressure difference $\Delta P_{ref}$. The resultant pressure difference will thus be $\Delta P_{min}$, and the corresponding final updated $Q_{maxi}$ value will be $Q_{max}$. Furthermore, at the end of this second sequence, the last valve closed during this sequence, or if none are closed, the last valve closed during the first sequence, when opened, defines, if the flow velocities are appropriately selected, that set of one or more valves which results in a pressure difference which is the least above the reference pressure difference $\Delta P_{ref}$. Thus, the resultant pressure difference will be $\Delta P_{max}$ and the corresponding final updated $Q_{mini}$ value will be $Q_{min}$.

The first and second phases of the first operating procedure thus result in the desired $Q_{max}$ and $Q_{min}$ values from which the second operating procedure can determine the porosity $P_r$ of the material 3. Moreover, as is apparent, the activating pattern defined by these phases operates to minimize the required steps needed to arrive at these values. As a result, the pattern considerably reduces the time of operation of the unit 51.

Having briefly summarized the first operating procedure of the flow chart of FIGS. 2A and 2B, a more complete discussion of the entire procedure will now be given. More particularly, as above-indicated, the first operating procedure includes ten basic operating steps some of which may or may not be carried out depending upon the detected conditions. The step 101 is the initial operating step wherein the reset switch 54 of the unit 51 is actuated, thereby causing the unit to condition the signals $e_A$ through $e_L$ to cause the members 18-A through 18-L to close the valves 17-A through 17-L. These valves are then closed and step 102 is instituted by depressing start switch 52. This, in turn, provides start signals to the processing unit 51 and to the actuating member 21. The latter, thereupon, actuates valve assembly 22, causing cylinder 23 to move terminal manifold section 7-C into engagement with area 3-A of material 3. Medium flow from output manifold 7 can now be applied and conveyed to the area.

The start signal input at the unit 51 thereupon actuates the remaining steps in the first operating procedure. The operating step 103 is thus instituted causing an output signal $e_V$ to be applied to a solid state relay 56 which connects a power source (not shown) to the actuating member 15-C of valve 15. In response thereto, member 15-C causes the atmospheric pressure input to valve section 15-B to be coupled to the valve output 15-D and to be sensed by the pressure transducer 37. The sensed pressure is then converted into a digital signal by passage through demodulator 36 and analog-to-digital converter 38 and inputed to processing unit 51. This signal is then stored by the unit 51 which now removes the signal $e_V$. Thereupon, the actuating member 15-C releases closing valve section 15-B and opening valve section 15-A. This couples the flow in the input manifold 6 to pressure transducer 37 which monitors the flow and generates a signal indicative of the flow pressure. This signal is continuously applied to the unit 51 again via demodulator 36 and analog-to-digital converter 38 via the signal $e_1$.

In the next operating step 104, the processing unit 51 sets to zero certain operating variables ($Q_{maxi}$ and $Q_{mini}$ included) to be used in the remaining steps of operation. The unit 51 then proceeds into the first valve activating phase instituted by operating step 105. In this operating step, the unit first conditions the output signals $e_A$ through $e_L$ so that the signal $e_A$ causes the actuating member 18-A to open the valve 17-A. Medium flow is then coupled from the input manifold 6 through valve 17-A and orifice member 16-A to the output manifold 7. The manifold 7 conveys this medium flow to the area 3-A of the material 3, thereby creating the pressure difference $\Delta P$.

The latter pressure difference, in turn, is fed to the unit 51 as digital signal $e_{\Delta P}$ via the transducer 34, demodulator 33 and analog-to-digital converter 32. The unit 51 then reads this pressure difference via the latter signal and also retrieves from memory the flow rate value $F_A$. It then compares the read pressure difference to the reference pressure difference. If the comparison shows the measured pressure difference is less than the reference, the signal $e_A$ is released closing valve 17-A. Thereupon, the procedure of opening a valve, monitoring and reading the pressure difference $\Delta P$ which results from opening the valve, reading the flow rate corresponding to the valve, and closing the valve if the measured pressure difference is less than the reference pressure difference is repeated in step 105 proceeding in sequence from the valve 17-B toward the valve 17-L.

The first time a particular opened valve results in a measured pressure difference greater than that of the reference, the comparison carried out in step 105, after reading the flow rate, will indicate this. Recognizing this condition, the unit 51 terminates the step 105, and the first activating phase is discontinued. The unit then moves to step 106 where the measured pressure difference is compared to a second higher reference pressure difference $\Delta P_{ref1}$ shown, illustratively, as a pressure equivalent to that exerted by a 20 centimeter column of water (20 cm). If the measured pressure difference is less than this second reference, the unit 51 moves to step 107, where it computes an initial intermediate value of $Q_{mini}$ from the measured pressure difference and the corresponding flow rate. Thereafter, the unit removes the output signal which causes the particular valve to close.

After closing of the valve, the unit 51 proceeds to the second valve activating phase instituted in step 108. In this operating step, the unit conditions the output signals so that the signal preceding the signal causing the termination of the step 105 will cause opening of its corresponding valve. Thus, for example, if opening of the valve 17-D corresponding to the signal $e_D$ caused termination of the step 105, the preceding signal $e_C$ is now conditioned to open its valve 17-C. Upon opening of the first valve in this second phase, the pressure difference across the area 3-A is again monitored and applied to the unit 51, while the associated flow rate is read. The unit 51 then again compares the measured pressure difference to the reference pressure difference $\Delta P_{ref}$ and if it does not exceed the reference value, the unit calculates an intermediate value of $Q_{maxi}$ from the measured pressure difference and the read flow rate. Thereafter, the unit maintains the output signals $e_A$ to $e_L$ conditioned so that the particular valve remains opened.

If, on the other hand, the measured pressure difference from opening the valve exceeds the reference pressure difference, then the unit, rather than calculating an intermediate $Q_{maxi}$ value, calculates an intermediate $Q_{mini}$ value from the measured pressure difference and corresponding flow velocity. This $Q_{mini}$ value is then stored in place of the $Q_{mini}$ value calculated in step 107. In this case, the unit then releases the output signal and the particular valve closes.

The unit 51 continues conditioning the output signals to open valves in descending flow rate order in step 108 and either calculates a new $Q_{maxi}$ if the resultant pressure difference from the opening of a particular valve is below the reference pressure difference or a new $Q_{mini}$ if the resultant pressure difference is above the reference pressure. In both cases, the value circulated is determined from the valve that is opened, and from the previously opened valves which have been retained opened and from the sum of the flow rates of the opened valves. In the former case, the opened valve is thereafter retained opened and in the latter case the opened valve is closed.

After the second valve activating phase of step 108 is complete, the final stored $Q_{maxi}$ will be equal to $Q_{max}$, since the pressure difference corresponding to this final value of $Q_{maxi}$ will be the least below the value of $\Delta P_{ref}$ for the given set of passage means. Likewise, the final stored $Q_{mini}$ value will be equal to $Q_{min}$, since the pressure difference corresponding thereto will be the least above the reference pressure difference as a result of appropriate selection of the flow rates of the passage means.

The unit 51 at the completion of step 108 has thus calculated values of $Q_{mini}$ and $Q_{maxi}$ equal to $Q_{min}$ and $Q_{max}$, respectively and, therefore, proceeds to the second operating procedure of step 109. In this step, it calculates the Coresta porosity of the material 3 and displays same on the display panel 55.

More particularly, in operating step 109, an initial check is made to determine whether both non-zero $Q_{maxi}$ and $Q_{mini}$ values have been determined. If such is the case, these values are averaged to provide the average volumetric flow per unit time per unit pressure drop $Q_{bar}$. Thereafter, $Q_{bar}$ is multiplied by the reference pressure difference $\Delta P_{ref}$ and divided by the extent of the area 3-A. The resultant value is the desired Coresta porosity $P_r$ of the paper 3 which is displayed on the panel 55. In the case shown, the porosity value is also corrected for any variations occurring in the input manifold pressure and atmospheric pressure by further including compensating multipliers $P_{manc}$ and $P_{barc}$ in its calculation. These values are derived from the stored value of the atmospheric pressure and the value of the manifold pressure which is read at this time from the signal $e_1$.

The first and second operating procedures of the flow diagram of FIGS. 2A and 2B are also provided with some additional operations for handling certain special operating conditions. Thus, if in step 105 the opening of none of the valves results in a measured pressure difference exceeding the reference pressure difference $\Delta P_{ref}$, then after the last valve is opened it is left opened and the unit proceeds to step 110. At this step, an intermediate value of $Q_{maxi}$ is calculated from the measured pressure and the corresponding flow rate of the opened valve. Thereafter, the unit proceeds directly to step 108 bypassing steps 106 and 107. Thus no intermediate $Q_{mini}$ value is calculated. If in step 108, the opening of the valves in descending order does not result in a pressure difference which exceeds the reference pressure difference then no value of $Q_{mini}$ is calculated in this step. As a result, when step 108 is completed and step 109 instituted, the check made for a non-zero value of $Q_{mini}$ indicates no non-zero value is present, the initial value of $Q_{mini}$ having been set at zero in step 104. Unit 51 recognizes this condition and displays on panel 55 an overrange signal indicating the porosity of the material is not within the range of the measuring structure 1.

Another special condition occurs when opening of a particular valve during step 105 causes a pressure difference which exceeds not only the reference $\Delta P_{ref}$, but, in addition, the second reference pressure difference $\Delta P_{ref1}$. In this case, the unit proceeds to step 111 and bypasses step 107. In step 111, the unit closes the particular valve and then computes a value of $Q_{mini}$ from the pressure difference and corresponding flow velocity of the immediately preceding valve. The unit 51 then proceeds to step 108 in the usual manner. It should be noted that if the valve causing the pressure difference above $\Delta P_{ref1}$ is the first valve opened in step 105, then step 108 does not proceed, and, therefore, no further $Q_{mini}$ is calculated. $Q_{mini}$ will thus have its initial zero value set in step 104. This will be recognized in step 109 as another overrange condition and will be displayed by the unit.

A further special condition occurs if during the step 108, opening of a valve results in a pressure difference which exceeds the second reference $\Delta P_{ref1}$. In this case, the particular valve is closed, no new value of $Q_{mini}$ is calculated, and the step continues in the usual manner. Finally, one other special condition occurs when the first opened valve in step 105 provides a pressure difference greater than $\Delta P_{ref}$, but less than $\Delta P_{ref1}$. In this case, there are no preceding valves to open in step 108 and the unit 51 institutes step 109 without having calculated a value of $Q_{maxi}$. $Q_{maxi}$ thus has as its value the initially set zero value of step 104. Upon checking for a non-zero $Q_{maxi}$ value in step 109, the unit recognizes that no such value has been calculated and then proceeds to set $Q_{maxi}$ equal to $Q_{mini}$. The step 109 thereafter proceeds as usual.

The operating procedure of FIGS. 2A and 2B has the further facility of being able to convert the calculated Coresta porosity $P_r$ into the Greiner porosity unit of measure as evidenced by the step 109. By suitable operation of a display switch (not shown) of the unit, the Greiner form of the porosity can be displayed instead of the Coresta form.

As above-noted, using the valve activation pattern of the flow diagram of FIGS. 2A and 2B will result in the generation of a $Q_{mini}$ value equal to $Q_{min}$ if the flow rates of the passage means valves are appropriately selected. Selection of the particular flow rates to ensure this condition will, of course, depend upon each particular application. In general, use of the abovementioned preferred flow rate ratio (i.e., 2.0) will provide this condition.

The above discussion of the operating procedure of the flow diagram of FIGS. 2A and 2B makes it quite apparent that implementation of the procedure on a conventional microprocessor of the type mentioned above is well within the purview of one of ordinary skill in the art. However, to further illustrate and facilitate use of the invention, an illustrative program for implementing the procedure of FIGS. 2A and 2B has been included at the end of this specification and has been labelled Appendix A.

As was discussed in detail hereinabove, the assembly 2 enables one or more of a plurality of medium flows of different increasing flow rates to be conveyed to the area 3-A of the material 3. FIGS. 3 through 6 show a form of the assembly 2 which is specifically adapted to promote rapid operation of the measuring structure 1.

Figure 3:
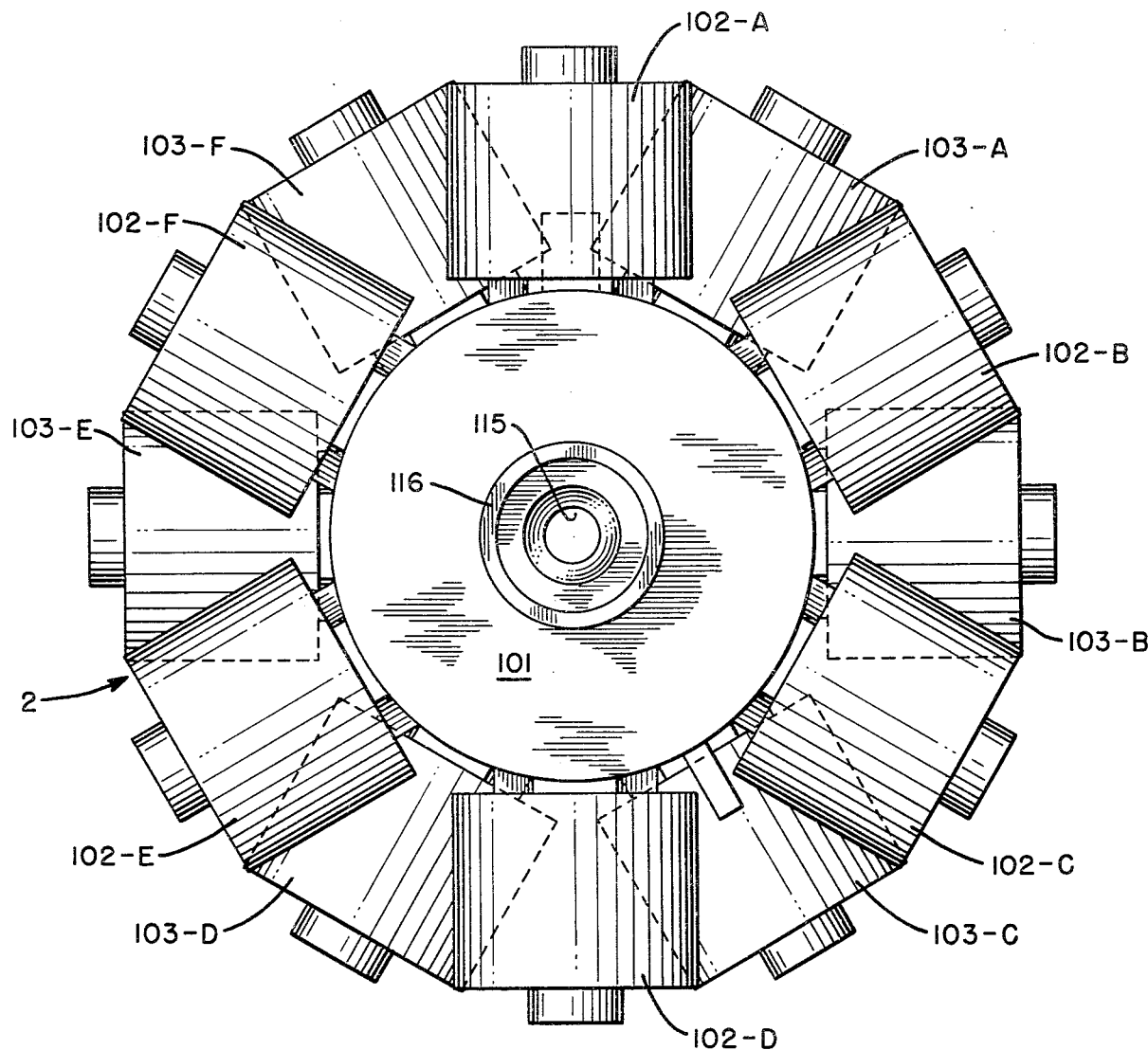
FIG. 3 shows a front elevational view of a composite medium flow generating and conveying assembly, which can be used with the measuring structure of FIG. 1.

The assembly 2 of FIG. 3 comprises a body 101, shown as having a cylindrical configuration, and around whose outer circumferential surface are arranged in interleaved relationship first and second groups of members 102-A through 102-F and 103-A through 103-F. As can be seen more clearly in FIG. 5 the two groups of members are situated about spaced circumferential lines or zones of the body. These groups of members form the openable passage means of the assembly 2 depicted as 5-A through 5-L in FIG. 1A.

The rear surface 104 of the body 1 is provided with an annular groove 105 into which extends a radial passage 105-A opening onto the outer surface of the body. Extending from the groove 105 into the interior of the body are two groups of interleaved axial grooves 106-A through 106-F and 107-A through 107-F. The first group of these grooves 106-A through 106-F extend to positions below the respective positions of members 102-A through 102-F and communicate via passages 108-A through 108-F with seating areas 109-A through 109-F provided in the body 1 for such members. Similarly, the second group of axial grooves 107-A through 107-F extend into the body 1 to a lesser extent than the grooves 106-A through 106-F so as to be positioned below the respective positions of members 103-A through 103-F. This second group of grooves communicates, via passages 112-A through 112-F with further seating areas 113-A through 113-F provided in the body 1 for seating the members 103-A through 103-F. The aforesaid passages, grooves and seating areas form the input manifold of the assembly 2 depicted as 6 in FIG. 1A.

Below the seating areas 109-A through 109-F extend radial channels 11-A and 111-F, respectively. Similarly, below the seating areas 113-A through 113-F extend further radial channels 114-A through 114-F. In FIG. 5, only axial grooves 106-A and 107-C and their corresponding passages 108-A and 112-C, seating areas 109-A and 113-C, and radial channels 111-A and 114-C are specifically illustrated.

The two groups of radial channels 111-A through 111-F and 114-A through 114-F enter a common axial groove 115. The groove 115 extends from the output end 116 of the body 1 axially to a position slightly beyond the position of the second group of radial channels 114-A through 114-F. The groove 115 forms the output manifold of the assembly 2 depicted as 7 in FIG. 1A.

The body 101 is also provided with passages 117 and 118 leading from the grooves 105 and 115 to the exterior of the body. These passages provide means for conveying the medium flows in their respective grooves to suitable transducers (37 and 34 in FIG. 1) provided for measuring the pressures of such flows.

Figure 6:
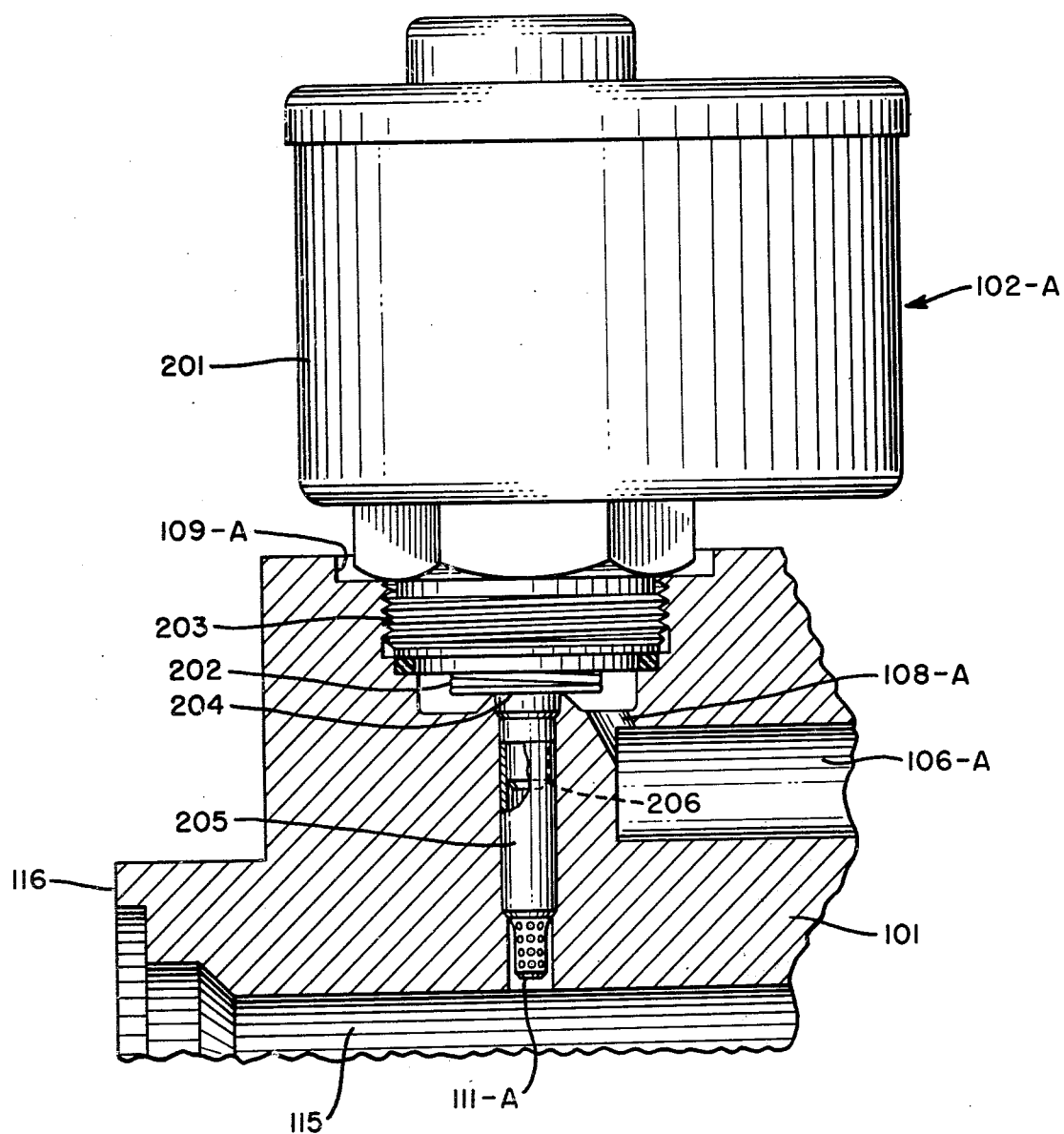
FIG. 6 illustrates a partial view partly in cross section of an actuating valve assembly seated in its corresponding section of the assembly of FIG. 4.

FIG. 6 shows the member 102-A seated in its respective seating area 109-A. As illustrated, the member is provided with an upper solenoid actuating body 201 which threadably engages via threads 203 the seating area 109-A. A valve portion 202 extends from the body and in the closed position of the member, seats on the upper edge 204 of the radial channel 111-A. Inserted within the channel is a nozzle 205 which is held in the channel by an expander 206 and which is configured so as to provide medium flow therefrom at a predetermined constant flow rate.

Movement of the valve portion 202 onto and off of the upper edge 204 of the channel 111-A is controlled by the solenoid actuating body 201 and closes and opens the flow path between the lower region of the seating area and the interior of the nozzle. Upon suitable activation of the body, this path can thus be opened and closed. Upon opening, medium entering the seating area will pass into the nozzle and out therefrom into the lower end of the passage 111-A at the predetermined constant flow rate.

Each of the remaining members 102-B through 102-F in the first group and each of the members 103-A through 103-F in the second group are of similar basic configuration and are disposed similarly in their respective seating areas as the member 102-A. However, the nozzles of these members are adapted to provide medium flows of different increasing flow rates. In the particular case shown, the flow rates provided by the members increase in going from members 102-A to 102-F and from members 103-A to 103-F.

Typically, each of the actuating bodies 201 can be a device manufactured by Automatic Switch Company under part No. 82001. The nozzles 205, on the other hand, can be of the type manufactured by The Lee Company and referred to as Lee hydraulic insert jets in the Technical Hydraulic Handbook distributed by such company.

As can be appreciated, the assembly 2 of FIGS. 3 to 6 enables the generation of medium flows of increasing flow rates and further enables the selective conveying of one or more of these flows to a common output conduit. More specifically, medium flow coupled into the body 1 through the input groove 105-A will be conveyed therefrom to the annular groove 105. From the groove 105, the medium will be coupled by the groups of axial grooves 106-A through 106-F and 107-A through 107-F to the respective seating areas 109-A through 109-F and 113-A through 113-F. Depending upon the activation state of the actuating body 201 arranged in a particular seating area, medium flow will or will not then be coupled from the seating area through the respective nozzle 205 of the member and from there to the output groove 115. If a particular member is in a state to permit such coupling, i.e., its actuating body has unseated its valve portion, then medium flow will be conveyed from the respective seating area through the respective nozzle and out therefrom at the predetermined flow rate.

While the dimensions of the passages, grooves, etc. in the body 101 can have varied values depending upon the particular application, it has been found advantageous to provide a volume for the output manifold, i.e., the groove 115, which is less than about 10 cubic centimeters. With this volume of the groove, a rapid response time for the measuring unit can be realized. In particular, a maximum response time of about 13 seconds is realizable when measuring the porosity of highly porous materials.

As above-indicated, the measuring structure of FIGS. 1A and 1B is capable of measuring porosities over an extremely wide band. More specifically, porosities over a band ranging from 15 to 40,000 Coresta have been successfully measured using a structure of the present type provided with 12 passage means. These passage means provided medium flows having the following nominal flow rates in cubic centimeters per minute: 50; 96; 175; 340; 415; 828; 1650; 3370; 6700; 13,500; 27,000; and 54,000. Moreover, the input manifold pressure of this structure was maintained at approximately 40 psia and the predetermined area 3-A was approximately two square centimeters.

In all cases, it is understood that the above-described arrangements are merely illustrative of the many possible specific embodiments which represent applications of the present invention. Numerous and varied other arrangements can readily be devised in accordance with the principles of the present invention without departing from the spirit and scope of the invention.

APPENDIX A

PL/M-80 COMPILER

ISIS-II PL/M-80 V3.0 COMPILATION OF MODULE POROS
OBJECT MODULE PLACED IN :F1:PORO2.OBJ
COMPILER INVOKED BY: PLM80 :F1:PORO2.PLM DEBUG PRINT(:LP:)

```
1           POROS: DO;
            $INCLUDE(PBBR.PLM)
      =     /* PLM ABBREVIATIONS INCLUDED */
      =     $NOLIST 11    1     DCL RTCOBUF (2) BYTE;
12    1     DCL J1CNTRLPORT LIT '0F7H';
13    1     DCL J2CNTRLPORT LIT '0EFH';
14    1     DCL CNTRLWORD1 LIT '081H';
15    1     DCL CNTRLWORD2 LIT '083H';
16    1     DCL LOWVLVES LIT '0F4H';
17    1     DCL HIVLVES LIT '0F5H';
18    1     DCL RCDOUTPUTS LIT '0EEH';
19    1     DCL RTCDINPUTS LIT '0EDH';
20    1     DCL UPPERATCDBITS LIT '0EEH';
21    1     DCL DISPLAYENABLES LIT '0ECH';
22    1     DCL STATUSINS LIT '0F5H';
23    1     DCL STATUSOUTS LIT '0F6H';
24    1     DCL FLG1 (43) BYTE DATA (83H, 6FH, 0, 0, 8C8H, 8CFH, 0, 0, 8C2H, 86EH, 1, 0,
                  8FCH, 6D9H, 2, 0, 12H, 81H, 3, 0, 88H, 8E9H, 6, 0, 26H, 84H, 8CH, 0,
                  83H, 59H, 12H, 0, 38H, 8A9H, 36H, 0, 18H, 8C9H, 62H, 3, 8C8H, 8C4H, 8D4H, 0, 80A2H, 8C9H, 8AFH, 1);
```

APPENDIX A CONT'D

PL/M-80 COMPILER

```
25  1    DCL CORT(GREIN (4) BYTE DATA (0A1H,25H,80H,6CH); /*425.77 FOR THE EQUATION
             GREINER = SQR((425.77/FINALDPNUM)**2 + (5.399)**2 ) */
26  1    DCL FLDGCOR (4) BYTE DATA (63H,08H,0,0); /* CONSTANT (5.399)**2 = 29.15*/
27  1    DCL H3NDRED (4) BYTE DATA (10H,27H,0,0);
28  1    DCL CONSTANT (4) BYTE DATA (64H,0,0,0); /*10.0 CM H2O AND CONSTANT 100 */
29  1    DCL CNTSPRCM (4) BYTE DATA (0,8,0,0); /* F.S. 20 CM=4096 CNTS */
30  1    DCL GREINNUM (4) BYTE;
31  1    DCL OUTOFRANGE (5) BYTE DATA (0,0BH,0CCH,0CAH,0H);
32  1    DCL FLOWSUM (4) BYTE;
33  1    DCL MASK LIT '0FH';
34  1    DCL RSSPCON (4) BYTE DATA (0,4,0,0); /* F.S. 40 PSIA = 4096 CNTS */
35  1    DCL QMAX (4) BYTE;
36  1    DCL QMIN (4) BYTE;
37  1    DCL DEBOUNCE LIT '100'; /* DEBOUNCE COUNT */
38  1    DCL FLAG BYTE;
39  1    DCL COUNT BYTE;
40  1    DCL X1 (4) BYTE EXT;
41  1    DCL X2 (4) BYTE EXT;
42  1    DCL BCDEF (5) BYTE EXT;
43  1    DCL I BYTE;
44  1    DCL J BYTE;
45  1    DCL K BYTE;
46  1    DCL ATODCK1 (2) BYTE;
47  1    DCL ATODCK2 (2) BYTE;
48  1    DCL DELTA (2) BYTE DATA (020H,0); /* 32/40960 = .08% F.S. */
49  1    DCL SCALER (2) BYTE DATA (0AH,0); /* MULT. BY 10 */
50  1    DCL VALUECHG BYTE;
51  1    DCL DELTA2 (4) BYTE;
52  1    DCL CONVERGE BYTE;
53  1    DCL MULTCON (2) BYTE DATA (05H,0);
54  1    DCL AVGCON (2) BYTE DATA (02H,0);
55  1    DCL GEAR (4) BYTE;
56  1    DCL PRESCK (4) BYTE;
57  1    DCL CONATMPRES (4) BYTE DATA (0E0H,05H,02H,00H); /*14.691 PSIA STANDARD
             ATMOSPHERIC PRESSURE REFERENCE*/
58  1    DCL ATMCHG (4) BYTE; /*CALCULATED % CHANGE IN ATM PRES*/
59  1    DCL PERCENTCHG (2) BYTE DATA (28H,0); /* 40 PSIA CONSTANT REF */
60  1    DCL DISPLAYCNT BYTE;
61  1    DCL FINALDPNUM (4) BYTE;
62  1    DCL DISBUF (10) BYTE;
63  1    DCL Z BYTE;
64  1    DCL P BYTE;
65  1    DCL Q BYTE;
66  1    DCL R BYTE;
67  1    DCL S BYTE;
68  1    DCL M BYTE;
69  1    DCL N BYTE;
70  1    DCL E BYTE;
71  1    DCL F BYTE;
72  1    DCL G BYTE;
73  1    DCL L BYTE;
74  1    DCL HIMARK (4) BYTE DATA (0C8H,0,0,0); /* 20 CM H2O OVERPRESSURE LIMIT */
75  1    DCL MNO BYTE;
76  1    DCL GFAKE (4) BYTE;
77  1    DCL TENTHOUSND (2) BYTE DATA (10H,27H);

78  1    ADDD: PROC EXT;
79  2    END ADDD;
```

APPENDIX A CONT'D

PL/M-80 COMPILER

```
80   1      MSUB: PROC EXT;
81   2      END MSUB;

82   1      MMPY: PROC EXT;
83   2      END MMPY;

84   1      MDIV: PROC EXT;
85   2      END MDIV;

86   1      LODX1D: PROC (PTR) EXT;
87   2        DCL PTR ADDR;
88   2      END LODX1D;

89   1      LODX2D: PROC (PTR) EXT;
90   2        DCL PTR ADDR;
91   2      END LODX2D;

92   1      STRX1D: PROC (PTR) EXT;
93   2        DCL PTR ADDR;
94   2      END STRX1D;

95   1      ZX1: PROC EXT;
96   2      END ZX1;

97   1      ZX2: PROC EXT;
98   2      END ZX2;

99   1      MSZCK: PROC EXT;
100  2      END MSZCK;

101  1      MSQRT: PROC EXT;
102  2      END MSQRT;

103  1      BIBCD: PROC EXT;
104  2      END BIBCD;

105  1      ZBCDBF: PROC EXT;
106  2      END ZBCDBF;

107  1      LODX1S: PROC (PTR) EXT;
108  2        DCL PTR ADDR;
109  2      END LODX1S;

110  1      LODX2S: PROC (PTR) EXT;
111  2        DCL PTR ADDR;
112  2      END LODX2S;

113  1      STRX1S: PROC (PTR) EXT;
114  2        DCL PTR ADDR;
115  2      END STRX1S;

116  1      FLASH: PROC;
117  2        DO Z=1 TO 5;
118  3          OUTPUT(BCDOUTPUTS)=000H;
119  3          OUTPUT(DISPLAYENABLES)=ROL(7FH,Z);
120  3          CALL TIME(80H);
121  3        END;
122  2        OUTPUT(BCDOUTPUTS)=0FFH;
```

APPENDIX A CONT'D

PL/M-80 COMPILER

```
123  2        OUTPUT(DISPLAYENABLES)=09FH;
124  2      END FLASH;

125  1      DELATMPRES: PROC;
126  2        CALL LODX2S(.TENTHOUSND);
127  2        CALL MPY;
128  2        CALL LODX2D(.ABSPCON);
129  2        CALL MDIV;
              /*NOW X1 CONTAINS DELTA P OF ATMOSPHERIC PRESS. TRANSDUCER IN PSIA */
130  2        CALL LODX2D(.CONATMPRES);
131  2        CALL MDIV;
132  2        CALL STRX1D(.ATMCHG);
133  2      END DELATMPRES;

134  1      DELTAABS: PROC;
135  2        CALL LODX2D(.CONSTANT);
136  2        CALL MPY;
137  2        CALL LODX2D(.ABSPCON);
138  2        CALL MDIV;
              /* X1 NOW CONTAINS DELTA P OF ABS PRESSURE TRANSDUCER IN PSIA */
139  2        CALL STRX1D(.PRESX);
140  2        CALL LODX2S(.PERCENTCHG);
141  2        CALL MDIV;
142  2        CALL LODX2D(.OBAR);
143  2        CALL MPY;
144  2      END DELTAABS;

145  1      DELAY: PROC (U);
146  2      DCL U ADDRESS;
147  2        DO L = 1 TO U;
148  3          CALL TIME(250);
149  3        END;
150  2      END DELAY;

151  1      NUMOUT: PROC;
152  2      DCL I BYTE;
153  2        DO I=0 TO 4;
154  3          DISBUF(2*I)=(BCDBF(I)AND 0F0H);
155  3          DISBUF((2*I)+1)=(ROL((BCDBF(I) AND 0FH),4));
156  3        END;
              /* BCDBF IS NOW UNPACKED INTO DISBUF (MSD,-,-,-,-,-,LSD) */
157  2        DISPLAYCNT=3;
158  2        FLAG = TRUE;
159  2        DO WHILE FLAG = TRUE;
160  3          IF DISBUF(DISPLAYCNT)0H THEN FLAG=FALSE;
162  3          ELSE IF DISPLAYCNT=5 THEN FLAG=FALSE;
164  3               ELSE DISPLAYCNT=(DISPLAYCNT+1);
165  3        END;
166  2      END NUMOUT;

167  1      AINDIN: PROC;
168  2        OUTPUT(STATUSOUTS)=(INPUT(STATUSINS) OR 80H);
169  2        OUTPUT(STATUSOUTS)=(INPUT(STATUSINS) AND 7FH);
170  2        FLAG = TRUE;
171  2        COUNT=0;
172  2        DO WHILE FLAG=TRUE;
173  3          IF(NOT(INPUT(STATUSINS)) AND 08H)= 08H
                 THEN COUNT=(COUNT + 1);
```

APPENDIX A CONT'D

PL/M-28 COMPILER

```
175   3              ELSE COUNT = 0;
176   3              IF COUNT = 3
                     THEN FLAG = FALSE;
178   3              END;
179   2         ATODBUF(0)=(NOT(INPUT(ATODINPUTS)));
180   2         ATODBUF(1)=(NOT(INPUT(UPPERATODBITS))AND MASK);
181   2      END ATODIN;

182   1      ATODSUM: PROC;
183   2         DO F=1 TO 10;
184   3             CALL ATODIN;
185   3             CALL LODX2S(.ATODBUF);
186   3             CALL DELAY(9);
187   3             CALL XADD;
188   3         END;
189   2         CALL FLASH;
190   2      END ATODSUM;

191   1      SIZER: PROC;
192   2         IF CARRY = FALSE
                THEN DO;
194   3             CALL MSUB;  /* X1=X2 PROCEED TO CALCULATE */
195   3             CALL LODX2S(.DELTA);
196   3             CALL MSZCK;
197   3             IF CARRY = TRUE THEN FLAG=FALSE; /* FLOW STABLE -- CALCULATE */
198   3                 ELSE FLAG=TRUE; /* FLOW NOT STABLE GET MORE READINGS */
200   3             END;
201   2         ELSE DO;
202   3             CALL LODX2D(.X1); /* X1<>X2 INTERCHANGE VALUES THEN CAL */
203   3             CALL LODX1S(.ATODCK2);
204   3             CALL MSUB;
205   3             CALL LODX2S(.DELTA);
206   3             CALL MSZCK;
207   3             IF CARRY = TRUE THEN FLAG=FALSE;
208   3                 ELSE FLAG= TRUE;
210   3             END;
211   2      END SIZER;

212   1      DISPLAY: PROC (T);
213   2      DCL T BYTE;
214   2         Z=5;
215   2            DO CASE (DISPLAYCNT-3);

216   3            DO P=DISPLAYCNT TO (DISPLAYCNT + 4);
217   4               OUTPUT(BCDOUTPUTS)= DISBUF(P);
218   4               OUTPUT(DISPLAYENABLES)=(ROL(7FH,Z) AND 09FH);
219   4               CALL TIME(T);
220   4               Z=(Z-1);
221   4               IF Z=0 THEN Z=5;
223   4               END;

224   3            DO P=DISPLAYCNT TO (DISPLAYCNT + 4);
225   4               OUTPUT(BCDOUTPUTS)= DISBUF(P);
226   4               OUTPUT(DISPLAYENABLES)=((ROL(7FH,Z)) AND 0DFH);
227   4               CALL TIME(T);
228   4               Z=(Z-1);
```

APPENDIX A CONT'D

PL/M-80 COMPILER

```
229  4          IF Z=0 THEN Z=5;
231  4          END;

232  3          DO P=DISPLAYCNT TO (DISPLAYCNT + 4);
233  4          OUTPUT(BCDOUTPUTS)= DISBUF(P);
234  4          OUTPUT(DISPLAYENABLES)=((ROL(7FH,Z)) AND 0BFH);
235  4          CALL TIME(T);
236  4          Z=(Z-1);
237  4          IF Z=0 THEN Z=5;
239  4          END;
240  3          END;
241  2          OUTPUT(BCDOUTPUTS)=0FFH;
242  2       END DISPLAY;

243  1       INDELTAP: PROC;
244  2          CALL ZX1;
245  2          CALL STRX15(.ATODCK1);
246  2          CALL STRX15(.ATODCK2);
247  2          FLAG = TRUE;
248  2          DO WHILE FLAG=TRUE;
249  3             CALL ZX1;
250  3             CALL DELAY(0);
251  3             CALL ATODSUM;
252  3             CALL STRX15(.ATODCK1);
253  3             CALL LODX2S(.ATODCK2);
254  3             CALL MSZCK;
255  3             CALL SIZER;
    /* SIZER CONTAINS THE STATUS OF FLAG. IF FLAG = TRUE THEN
       ANOTHER SET OF 10 READINGS WILL BE TAKEN AND THE PROGRAM
       WILL REMAIN IN THIS LOOP TAKING READINGS IN SETS OF 10
       TO DETERMINE IF THE FLOW HAS STABLIZED. IF IT HAS SIZER
       WILL MAKE THE FLAG=FALSE ALLOWING CALCULATIONS TO BEGIN */
256  3             CALL LODX15(.ATODCK1);
257  3             CALL STRX15(.ATODCK2);
    /* PUT THE OLD SET OF READINGS IN ATODCK2 AND REPLACE ATODCK1
       WITH THE NEW SET OF READINGS */
258  3          END;
259  2       END INDELTAP;

260  1       DELTADP: PROC;
261  2          CALL LODX2S(.SCALER);
262  2          CALL MPY;
263  2          CALL LODX2D(.CNTSPRCH);
264  2          CALL MDIV;
    /* X1 NOW CONTAINS DELTA P IN CM OF H2O */
265  2          CALL STRX1D(.DELTAP);
266  2          CALL LODX2D(.CONSTANT);
267  2          CALL MSZCK;
    /* IF DELTA P >= CONSTANT CARRY = FALSE
       IF DELTA P < CONSTANT CARRY = TRUE */
268  2       END DELTADP;

269  1       HITEST: PROC;
270  2          CALL LODX1D(.HIMARK);
271  2          CALL LODX2D(.DELTAP);
272  2          CALL MSZCK;
    /* IF HIMARK >= DELTAP THIS ROUTINE SETS CARRY=FALSE
       IF HIMARK < DELTAP THIS ROUTINE SETS CARRY=TRUE*/
273  2       END HITEST;
```

APPENDIX A CONT'D

PL/M-80 COMPILER

```
274  1    WAIT: PROC; /*THIS PROC WAITS FOR DELTAP TO GO BELOW 10.0 CM H2O
                        ONCE IT HAS GONE ABOVE 20.0 CM H2O */
275  2        MNO=FALSE;
276  2        DO WHILE MNO=FALSE;
277  3            CALL ZX1;
278  3            CALL ATODSUM;
279  3            CALL DELTADP;
280  3            IF CARRY = FALSE THEN MNO=FALSE;
282  3            ELSE MNO=TRUE;
283  3        END;
284  2    END WAIT;
```

/*************************************************
  **************************************************
  THIS IS NOW THE BEGINNING OF THE MAIN PROGRAM
       FIRST INITIALIZE THE 8255'S AND THEN ALL OUTPUTS
  **************************************************
  **************************************************/

```
285  1    OUTPUT(J1CNTRLPORT)=CNTRLWORD1;
286  1    OUTPUT(J2CNTRLPORT)=CNTRLWORD2;
287  1    OUTPUT(LOVALVES)= 00H;
288  1    OUTPUT(STATUSOUTS) = 010H;
289  1    OUTPUT(BCDOUTPUTS) = 0FFH;
290  1    OUTPUT(DISPLAYENABLES) = 09FH;
291  1    OUTPUT(HIVALVES) = 00H;

/* CHECK FOR FOOTSWITCH CLOSE THEN OPEN TRANSITION TO START CONVERS. */
292  1    FLAG = TRUE;
293  1    COUNT = 0;
294  1    DO WHILE FLAG = TRUE;
295  2        IF (INPUT(STATUSINS)AND 01H) = 01H
                  THEN COUNT = (COUNT +1);
297  2            ELSE COUNT = 0;
298  2        IF COUNT = DEBOUNCE THEN FLAG = FALSE;
300  2    END;
301  1    FLAG = TRUE;
302  1    COUNT = 0;

303  1    DO WHILE FLAG= TRUE;
304  2        IF ( NOT(INPUT(STATUSINS))AND 01H) = 01H
                  THEN COUNT = (COUNT + 1);
306  2            ELSE COUNT = 0;
307  2        IF COUNT = DEBOUNCE THEN FLAG = FALSE;
309  2    END;
310  1    OUTPUT(HIVALVES)=10H; /* TURN ON PAPER HOLDER SOLENOID */

311  1    CALL DELAY(25); /* DELAY SO PAPERHOLDER HAS TIME TO CLOSE */

/* INITIALIZE ALL VALUES */

312  1    CALL ZX1;
313  1    CALL STRX10(.QMIN);
314  1    CALL STRX10(.QMAX);
315  1    CALL STRX10(.QPAKE);
316  1    CALL STRX10(.FLOWSUM);
```

APPENDIX A CONT'D

PL/M-80 COMPILER

```
317  1      CALL INDELTAP;
318  1      CALL DELTAPRES;
319  1      OUTPUT(STATUSOUTS) = 020H;
320  1      OUTPUT(HIVALVES) = 030H; /* TURN ON ABS PRES VALVE TO DISPLAY BLOCK
            ABS PRESSURE UNTIL RESET.  IN WAIT MODE DISPLAY WILL
            SHOW BAROMETRIC PRESSURE (40 PSIA=1.999 VOLTS) */

321  1      VALVECNT = TRUE;
322  1      S=1;
323  1      I=0;
324  1      DO WHILE VALVECNT = TRUE;
325  2          S=(S + 1);
326  2          I = (I + 1);
327  2          R=((I-1)*4);
328  2          CALL FLASH;

329  2          P= (0 XOR 0);
330  2          OUTPUT(LOVALVES)= LOW(SCL(8000H,S));
331  2          P = (0 XOR 0);
332  2          OUTPUT(HIVALVES)=( (INPUT(HIVALVES)AND 030H) OR (HIGH(SCL(8000H,S))));
333  2          CALL INDELTAP;
334  2          CALL DELTADP;
335  2          IF CARRY = FALSE
                THEN DO;
337  3              CALL HITEST;
338  3              IF CARRY = FALSE
                    THEN DO;
340  4                  CALL LODX1D(.FLOW(R));
341  4                  CALL LODX2D(.DELTAP);
342  4                  CALL MDIV;
343  4                  CALL STRX1D(.QMIN);
344  4                  OUTPUT(LOVALVES) = 00H;
345  4                  OUTPUT(HIVALVES) = (INPUT(HIVALVES)AND 030H);
346  4                  VALVECNT=FALSE;
347  4                  END;
348  3              ELSE DO;
349  4                  OUTPUT(LOVALVES) = 00H;
350  4                  OUTPUT(HIVALVES) = (INPUT(HIVALVES)AND 030H);
351  4                  CALL WAIT;
352  4                  CALL LODX1D(.QFAKE);
353  4                  CALL STRX1D(.QMIN);
354  4                  VALVECNT = FALSE;
355  4                  END;
356  3          END;
357  2          ELSE VALVECNT = TRUE;
358  2          CALL LODX1D(.FLOW(R));
359  2          CALL LODX2D(.DELTAP);
360  2          CALL MDIV;
361  2          CALL STRX1D(.QFAKE);

362  2          IF VALVECNT=TRUE
                THEN IF I = 12
                    THEN DO;
365  3                  CALL LODX1D(.FLOW(44));
366  3                  CALL STRX1D(.FLOWSUM);
```

APPENDIX A CONT'D

PL/M-80 COMPILER

```
367  3              CALL LOOX2D(.DELTAP);
368  3              CALL MDIV;
369  3              CALL STRX1D(.QMAX);
370  3              VALVECNT=FALSE;
371  3                 END;
372  2            ELSE VALVECNT=TRUE;
373  2         ELSE VALVECNT=FALSE;
374  2  END;

375  1  J = 0;
376  1  K = (I - 1);
377  1  CONVERGE = TRUE;

378  1  DO WHILE CONVERGE = TRUE;
379  2     J = (J + 1);
380  2     CALL FLASH;
381  2     IF J<K THEN GOTO FLAGTESTS;
382  2     N = (I - J);
383  2     M = ((N-1)*4);
384  2     P = (Q XOR Q);
385  2     OUTPUT(LOVALVES) = (LOW(SCL(2000H,(N+1)))OR (INPUT(LOVALVES)));
386  2     P = (Q XOR Q);
387  2     OUTPUT(HIVALVES)=(INPUT(HIVALVES) OR (HIGH(SCL(2000H,(N+1)))));
388  2     CALL INDELTAP;
389  2     CALL DELTACP;
390  2     IF CARRY = FALSE
              THEN DO;
391  3        CALL HITEST;
392  3        IF CARRY = FALSE
                 THEN DO;
393  4           CALL LOOX1D(.FLOWSUM);
394  4           CALL LOOX2D(.FLOW(N));
395  4           CALL MADD;
396  4           CALL LOOX2D(.DELTAP);
397  4           CALL MDIV;
398  4           CALL STRX1D(.QMIN);
399  4           P = (Q XOR Q);
400  4           OUTPUT(LOVALVES)=(INPUT(LOVALVES)AND(LOW(SCL(0FFFFH,N))));
401  4           P=(Q XOR Q);
402  4           OUTPUT(HIVALVES)=(INPUT(HIVALVES)AND(HIGH(SCL(0FFFFH,N))));
403  4           END;
404  3        ELSE DO;
405  4           P=(Q XOR Q);
406  4           OUTPUT(LOVALVES)=(INPUT(LOVALVES)AND(LOW(SCL(0FFFFH,N))));
407  4           P=(Q XOR Q);
408  4           OUTPUT(HIVALVES)=(INPUT(HIVALVES)AND(HIGH(SCL(0FFFFH,N))));
409  4           CALL WAIT;
410  4           END;
411  3        END;
412  2     ELSE DO;
413  3        CALL LOOX1D(.FLOWSUM);
414  3        CALL LOOX2D(.FLOW(N));
415  3        CALL MADD;
416  3        CALL STRX1D(.FLOWSUM);
417  3        CALL LOOX2D(.DELTAP);
418  3        CALL MDIV;
419  3        CALL STRX1D(.QMAX);
420  3        END;
421  2     END;
           /* TEST TO SEE IF QMIN = 0.0 (OUT OF RANGE) */
```

APPENDIX A CONT'D

PL/M-80 COMPILER

```
425   1    FLAGTESTS: CALL ZX1;
426   1         CALL LODX2D(.QMIN);
427   1         CALL MSZCK;
428   1         IF CARRY = FALSE
                THEN DO;
429   2            CALL MOVE(5,.OUTOFRANGE,.BCDBF);
430   2            CALL NUMOUT;
431   2            R=FALSE;
432   2            DO WHILE R=FALSE;
433   3               CALL DISPLAY(17H);
434   3               OUTPUT(BCDOUTPUTS)=0FFH;
435   3               CALL DELAY(9);
436   3               R=FALSE;
437   3            END;
438   2         END;

/* TEST TO SEE IF QMAX = 0.0 */
439   1    CALL ZX1;
440   1    CALL LODX2D(.QMAX);
441   1    CALL MSZCK;
442   1    IF CARRY = FALSE
443   1    THEN DO;
445   2       CALL LODX1D(.QMIN);
446   2       CALL STRX1D(.QMAX);
447   2       END;

448   1    OUTPUT(STATUSOUTS)=010H; /* CHANGE THE A TO D INPUT TO ABS PRESSURE
                                       TRANSDUCER NOT DELTA P TRANSDUCER */
449   1    CALL LODX1D(.QMAX);
450   1    CALL LODX2D(.QMIN);
451   1    CALL MADD;
452   1    CALL LODX2S(.MULTCON); /* (5(QMIN + QMAX)) */
453   1    CALL MMPY;
454   1    CALL STRX1D(.QBAR);
455   1    CALL INDELTAP;
456   1    CALL DELTAABS; /* QBAR IS ADJ. IF THERE IS ANY CHANGE IN ABS. PRES. */
457   1    CALL LODX2D(.CONSTANT); /* SCALE QBAR TO XXXXXXX.XX */
458   1    CALL MDIV;
459   1    CALL LODX2D(.ATMCHG);
460   1    CALL MMPY;
461   1    CALL LODX2D(.CONSTANT);
462   1    CALL MDIV;
463   1    CALL STRX1D(.FINALDPNUM);
464   1    CALL LODX2D(.HUNDRED);
465   1    CALL MSZCK;
           /*IF CORESTA VALUE (FINALDPNUM) >= HUNDRED CARRY=FALSE */
466   1    IF CARRY = FALSE
           THEN DO;

/* IF FINALDPNUM IS GREATER THAN 100 GREINERNUM = 0.00 */

468   2       CALL ZX1;
469   2       CALL STRX1D(.GREINRNUM);
470   2       END;

471   1    ELSE DO;
472   2       CALL LODX1D(.FINALDPNUM);
473   2       CALL LODX2D(.X1);
474   2       CALL MMPY;
```

APPENDIX A CONT'D

```
PL/M-80 COMPILER 475  2    CALL  LOOX2D(.CONSTANT);
476  2    CALL  MDIV;
477  2    CALL  LOOX2D(.X1);
478  2    CALL  LOOX1D(.CORTOGREIN);
479  2    CALL  MDIV;
480  2    CALL  LOOX2D(.FUDGCOR);
481  2    CALL  MPCD;
          /* X1 CONTAINS NUMBER FOR SQUARE ROOT TO BE TAKEN */
482  2    CALL  MSQRT;
483  2    CALL  LOOX2S(.SCALER);
484  2    CALL  MMPY;
          /* X1 CONTAINS GREINER NO. IN FORM XXX99XX.XX */
485  2    CALL  STRX1D(.GREINNUM);
486  2    END;
487  1    P = TRUE;
488  1    DO WHILE P = TRUE;
489  2    IF (INPUT(STATUSINS)AND 02H)= 02H /*BIT=1 GREINER, BIT=0 CURESTA */
          THEN CALL LOOX1D(.GREINNUM);
491  2    ELSE CALL LOOX1D(.FINALDPNUM);
492  2         CALL  BIBCD;
493  2         CALL  NUMOUT;
494  2         CALL  DISPLAY(17H);
495  2         P = TRUE;
496  2    END;

497  1    END POROS;

MODULE INFORMATION:

CODE AREA SIZE     = 085FH    2143D
    VARIABLE AREA SIZE = 0058H      88D
    MAXIMUM STACK SIZE = 0008H       8D
    586 LINES READ
    0 PROGRAM ERROR(S)

END OF PL/M-80 COMPILATION
```

What is claimed is:

1. Apparatus for measuring the porosity of a material comprising:
   means for measuring the pressure difference across a predetermined area of said material;
   means for generating and conveying to said area a plurality of medium flows having different predetermined volumetric flow rates;
   and control means responsive to said pressure measuring means for controlling said generating and conveying means and for determining said porosity employing said flow rates.

2. Apparatus in accordance with claim 1 wherein:
   said control means controls said generating and conveying means to generate and convey to said area a first set of one or more of said medium flows which results in a first measured pressure difference which is below a predetermined pressure difference to a lesser degree than the pressure difference which would result from any other set of one or more of said medium flows.

3. Apparatus in accordance with claim 2 wherein:
   said control means further controls said generating and conveying means to generate and convey to said area a second set of one or more of said medium flows which results in a second measured pressure difference which is above said predetermined pressure difference to a lesser degree than the pressure difference which would result from any other set of one or more of said medium flows.

4. Apparatus in accordance with claim 3 wherein:
   said control means includes means for determining said porosity employing the flow rates of said first and second sets of medium flows.

5. Apparatus in accordance with claim 4 wherein:
   said porosity determining means further employs said first and second measured pressure differences for determining said porosity.

6. Apparatus in accordance with claim 1 wherein:
   said control means includes means for controlling said means for generating and conveying so as to provide the generation and conveyance of medium flows and the termination of said generated and conveyed medium flows in accordance with a predetermined pattern.

7. Apparatus in accordance with claim 6 wherein:
said means for controlling in accordance with said predetermined pattern comprises:
means for terminating a particular generated and conveyed medium flow whenever that medium flow causes the pressure difference measured by said measuring means to exceed a predetermined pressure difference.

8. Apparatus in accordance with claim 7 wherein:
said means for controlling in accordance with said predetermined pattern further comprises:
means for generating and conveying to said area said medium flows in a first sequence of medium flows of increasing flow rate;
means for terminating each of said generated and conveyed medium flows in said first sequence prior to the conveyance of the next medium flow of that sequence;
means for terminating said generating and conveying of said medium flows in said first sequence when any one of said generated and conveyed medium flows causes the pressure difference measured by said measuring means to exceed said predetermined pressure difference;
means responsive to said termination of said generating and conveying of said medium flows in said first sequence for generating and conveying said medium flows in a second sequence of medium flows of decreasing flow rate starting with the medium flow whose flow rate is immediately below that of the medium flow which resulted in said termination;
and means for maintaining the generation and conveyance of said medium flows of said second sequence for the remainder of said second sequence unless terminated as a result of causing said measured pressure difference to exceed said predetermined pressure difference.

9. Apparatus in accordance with claim 8 wherein:
said control means further includes:
means for determining said porosity employing the flow rates corresponding to first and second sets of one or more medium flows;
said first set of one or more medium flows conprising the one or more medium flows of said second sequence which remain generated and conveyed;
and said second set of one or more medium flows comprising the one or more medium flows generated and conveyed during the generation and conveyance of the last medium flow to be terminated for causing said pressure difference measured by said measuring means to exceed said predetermined pressure.

10. Apparatus in accordance with claim 9 wherein:
said porosity determining means further employs the first and second measured pressure differences corresponding to said first and second sets of one or more medium flows to determine said porosity.

11. Apparatus in accordance with claim 10 wherein:
said porosity determining means includes:
means for forming a first sum of the flow rates of said first set;
means for forming a second sum of the flow rates of second set;
means for forming a first quotient of said first sum and said first measured pressure difference;
means for forming a second quotient of said second sum and said second measured pressure difference;
and means for averaging said first and second quotients.

12. Apparatus in accordance with claim 11 wherein:
said porosity determining means further includes;
means for forming a third quotient of said average and said predetermined area;
and means for forming the product of said third quotient and said predetermined pressure.

13. Apparatus in accordance with claim 12 wherein:
said porosity is the Coresta porosity of said material;
and said predetermined pressure is equivalent to the pressure exerted by a 10 centimeter column of water.

14. Apparatus in accordance with claim 1 wherein:
said means for generating and conveying comprises:
a plurality of openable passages means each for generating and conveying a different one of said plurality of medium flows and each having an input end for receiving a medium under pressure and an output end for conveying its respective medium flow;
supply means for coupling said medium under pressure to the input end of each of said plurality of passage means;
and means for coupling the generated medium flows at the output end of each of said passage means to said predetermined area of said material; and said control means comprises:
passage control means responsive to said pressure measuring means for generating signals for causing selective opening and closing of said plurality of openable passage means so as to permit and inhibit medium flow between the input and output ends of said plurality of openable passage means.

15. Apparatus in accordance with claim 14 wherein:
each of said plurality of passage means includes:
an orifice member connected between the input end and the output end of that passage means and adapted to provide at the output end of that passage means medium flow at a predetermined flow velocity;
and valve means for permitting and inhibiting flow through the orifice member of that passage means;
and said signals of said passage control means cause selective opening and closing of said valve means of said plurality of passage means.

16. Apparatus in accordance with claim 15 wherein:
the valve means of each of said plurality of passage means is connected between the input end of that passage means and the orifice member of that passage means.

17. Apparatus in accordance with claim 16 wherein:
the valve means of each of said plurality of passage means includes a solenoid valve.

18. Apparatus in accordance with claim 15 wherein:
said supply means comprises:
an input manifold adapted to provide said medium under pressure;
said means for coupling comprises:
an output manifold having an output end adapted to couple medium flow to said predetermined area; and the input end of each of said plurality of passage means is in communication with said input manifold and the output end of each of said passage means is in communication with said output manifold.

19. Apparatus in accordance with claim 18 wherein:
said generating and conveying means comprises;
a body member;
said body member having an first groove extending into said body member from an end thereof, said first groove comprising said input manifold;
and said body member having a second groove extending into said body member from an end thereof, said second groove comprising said output manifold.

20. Apparatus in accordance with claim 19 wherein:
each of said openable passage means is supported by said body.

21. Apparatus in accordance with claim 20 wherein:
said openable means are arranged in first and second groups around the circumference of said body.

22. Apparatus in accordance with claim 21 wherein:
said first and second groups are arranged around first and second circumferential zones of said body.

23. Apparatus in accordance with claim 21 wherein:
said openable passage means of said first group are interleaved between the openable passage means of said second group.

24. Apparatus in accordance with claim 20 wherein:
said body has a plurality of seating areas each for receiving the valve means of a different one of said plurality of passage means, said seating areas each opening onto the outer surface of said body and extending into said body;
said body has a first plurality of passages each of which leads from a different one of said seating areas to said first groove;
said body has a second plurality of passages each for receiving the orifice member of a different one of said plurality of passage means and extending between said second groove and the seating area receiving the valve means of that passage means.

25. Apparatus in accordance with claim 19 wherein:
the volume of said output manifold from said open end to the point at which the output end of the passage means whose output end is farthest from said open end enters said manifold is equal to or less than 10 cubic centimeters.

26. Apparatus in accordance with claim 1 or 10 wherein:
the ratio of each of said flow rates to the flow rate of immediately lower value is within the approximate range of 1.5 to 3.0.

27. Apparatus in accordance with claim 26 wherein:
the ratio of each of said flow rates to the flow rate of immediately lower value is approximately equal to 2.0.

28. Apparatus in accordance with claim 27 wherein:
said means for generating and conveying generates and conveys 12 medium flows.

29. A method of measuring the porosity of a material comprising the steps of:
measuring the pressure difference across a predetermined area of said material;
selectively generating and conveying to said area in dependence on said measured pressure difference a plurality of medium flows having different predetermined volumetric flow rates;
and determining said porosity employing said flow rates.

30. A method in accordance with claim 29 wherein:
said step of selectively generating and conveying comprises:
generating and conveying to said area a first set of one or more of said medium flows which results in a first measured pressure difference which is below a predetermined pressure difference to a lesser degree than the pressure difference which would result from any other set of one or more of said medium flows.

31. A method in accordance with claim 30 wherein:
said step of selectively generating and conveying further comprises:
generating and conveying to said area a second set of one or more of said medium flows which results in a second measured pressure difference which is above said predetermined pressure difference to a lesser degree than the pressure difference which would result from any other set of one or more of said medium flows.

32. A method in accordance with claim 31 wherein:
said step of determining said porosity is carried out employing the flow rates of said first and second sets of medium flows.

33. A method in accordance with claim 32 wherein:
said step of determining said porosity is further carried out employing first and second measured pressure differences.

34. A method in accordance with claim 29 wherein:
said step of selectively generating and conveying includes:
generating and conveying medium flows and terminating said generated and conveyed medium flows in accordance with a predetermined pattern.

35. A method in accordance with claim 34 wherein:
said step of generating and conveying in accordance with said predetermined pattern comprises:
terminating a particular generated and conveyed medium flow whenever that medium flow causes the pressure difference measured by said measuring means to exceed a predetermined pressure difference.

36. A method in accordance with claim 35 wherein:
said step of generating and conveying in accordance with said predetermined pattern further comprises:
generating and conveying said medium flows in a first sequence of medium flows of increasing flow rate;
terminating each of said generated and conveyed medium flows in said first sequence prior to the conveyance of the next medium flow of that sequence;
terminating said generating and conveying of said medium flows in said first sequence when any one of said generated and conveyed medium flows causes the pressure difference measured by said measuring means to exceed said predetermined pressure difference;
subsequent to terminating said generating and conveying of said medium flows in said first sequence generating and conveying said medium flows in a second sequence of medium flows of decreasing flow rate starting with the medium flow whose flow rate is immediately below that of the medium flow which resulted in said termination;
and maintaining the generation and conveyance of said medium flows of said second sequence for the remainder of said second sequence unless terminated as a result of causing said measured pressure difference to exceed said predetermined pressure difference.

37. A method in accordance with claim 36 wherein: said step of determining said porosity is carried out employing the flow rates corresponding to first and second sets of one or more medium flows, said first set of one or more medium flows comprising said one or more medium flows of said second sequence which remain generated and conveyed, and said second set of one or more medium flows comprising said one or more medium flows generated and conveyed during the generation and conveyance of the last medium flow to be terminated for causing said pressure drop measured by said measuring means to exceed said predetermined pressure.

38. A method in accordance with claim 37 wherein: said step of determining said porosity is further carried out employing first and second measured pressure differences corresponding to said first and second sets of one or more medium flows.

39. A method in accordance with claim 38 wherein: said step of determining said porosity includes:
    forming a first sum of the flow rates of said first set;
    forming a second sum of the flow rates of said second set;
    forming a first quotient of said first sum and said first measured pressure difference;
    forming a second quotient of said second sum and said second measured pressure difference;
    and averaging said first and second quotients.

40. A method in accordance with claim 39 wherein: said step of determining said porosity further includes:
    forming a third quotient of said average and said predetermined area;
    and forming a first product of said third quotient and said predetermined pressure.

41. A method in accordance with claim 40 further comprising:
    measuring the prevailing barometric pressure;
    forming a fourth quotient of said measured barometric pressure and a predetermined barometric pressure;
    measuring the pressure at an inlet manifold providing medium flow from which said plurality of medium flows can be generated and conveyed;
    forming a fifth quotient of said measured inlet manifold pressure and a predetermined reference pressure;
    and forming a second product of said first product and said fourth and fifth quotients.

42. A method in accordance with claim 41 wherein: said porosity value is the Coresta porosity of said material;
    and said predetermined pressure is equivalent to the pressure exerted by a 10 centimeter column of water.

43. A method in accordance with claim 29 or 38 wherein:
    the ratio of each of said flow rates to the flow rate of immediately lower value is within the approximate range 1.5 to 3.0.

44. A method in accordance with claim 43 wherein:
    the ratio of each of said flow rates to the flow rate of immediately lower value is approximately equal to 2.0.

* * * * *